(12) United States Patent
Zhang et al.

(10) Patent No.: US 11,730,153 B1
(45) Date of Patent: Aug. 22, 2023

(54) MANAGEMENT AND DISTRIBUTION DEVICE FOR INSECT BREEDING

(71) Applicant: SHENZHEN WINDBELL TECHNOLOGY CO., LTD., Shenzhen (CN)

(72) Inventors: Feng Zhang, Jiaxing (CN); Neng Xiong, Shenzhen (CN)

(73) Assignee: SHENZHEN WINDBELL TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 18/079,582

(22) Filed: Dec. 12, 2022

(30) Foreign Application Priority Data

Oct. 19, 2022 (CN) .......................... 202211283262.4

(51) Int. Cl.
*A01K 67/033* (2006.01)

(52) U.S. Cl.
CPC ...... *A01K 67/033* (2013.01); *A01K 2227/706* (2013.01)

(58) Field of Classification Search
CPC .................................................... A01K 67/033
USPC ......................................................... 119/6.5, 5
See application file for complete search history.

(56) References Cited

U.S. PATENT DOCUMENTS

2006/0266292 A1* 11/2006 Duckworth .......... A01K 1/0245
119/6.5

* cited by examiner

*Primary Examiner* — Yvonne R Abbott-Lewis
(74) *Attorney, Agent, or Firm* — Daniel M. Cohn; Howard M. Cohn

(57) ABSTRACT

A management and distribution device for insect breeding includes a main body, an upper cover, and a lower cover. The upper cover is clamped to a top portion of the main body, and the lower cover is clamped to a lower end of the main body. Three partition plates for insects to climb are clamped in an inner portion of the main body, and the three partition plates are wave-shaped. A notch is defined at a lower middle portion of each of the three partition plates, a plurality of through holes for insect faeces to pass through are defined on a bottom of the main body, an insertion opening is defined at a lower end of an outer wall of the main body, and a hinge door is rotatably disposed at the lower end of the outer wall of the main body.

10 Claims, 5 Drawing Sheets

MANAGEMENT AND DISTRIBUTION DEVICE FOR INSECT BREEDING

TECHNICAL FIELD

The present disclosure relates to a technical field of insect breeding management, and in particular to a management and distribution device for insect breeding.

BACKGROUND

With the development of modern science and technology, insects are not only the focus of human research and utilization in conventional fields, but also become the focus of the human research and utilization in a field of emerging science, the human research and utilization include aspects from utilization of insect bodies to utilization of insect functions, insect microorganisms, and insect genes. Most of the insects are bred in a breeding room without special equipment, as long as there is sufficient light in the breeding room and air circulates in the breeding room, work of breeding the insects may be smoothly carried on. Common equipment used in the breeding room is various due to different living habits of the insects.

After research, Chinese patent application No. 201820514913.9 discloses an insect breeding device, including a panel, a side plate, a breathable gauze, and an anti-escaping cuff for insects. An operation hole is defined in a middle of the panel, and fixing holes are defined on edges of the panel. A first end of the side plate is connected with a side end of a rear plate through the fixing holes and fixing pins, and a second end of the side plate is disposed on the panel. A bottom of the panel, a bottom of the side plate, and a bottom of the rear plate are connected with a side end of a bottom plate through the fixing holes and the fixing pins. Moreover, a rubber ring is sleeved at a joint of each of the fixing holes and each of the fixing pins, air holes are defined on both the side plate and the rear plate, and the breathable gauze is fixed to a top plate through a double-sided adhesive tape. The top plate is disposed on an upper end of the panel, an upper end of the side plate, and an upper end of the rear plate. An anti-escaping ring for the insects is disposed at one end of the anti-escaping cuff for the insects, and a groove is defined on the anti-escaping ring for the insects. The insect breeding cage is low in manufacturing cost, clean and hygienic, convenient for cleaning, and can directly observe growing situation of the insects.

However, the insect breeding cage is simple in structure and function and brings a poor breeding environment for the insects, which may easily increase a death rate of the insects and further increases time and energy cost of breeding the insects. Therefore, it is urgent to provide a refined management for insect breeding and it is necessary to propose a management and distribution device for insect breeding.

SUMMARY

The present disclosure aims to provide a management and distribution device for insect breeding having a more practical structure, which is complete in functions. The management and distribution device for insect breeding improves insect breeding environment and decreases a death rate of insects and time and energy cost of breeding the insects through integrating storage, feeding and breeding, faeces management, and convenient and fast putting of the insets to solve the problems mentioned in the background.

In order to achieve the aims, the present disclosure provides the management and distribution device for insect breeding, including a main body, an upper cover, and a lower cover. The upper cover is clamped to a top portion of the main body, and the lower cover is clamped to a lower end of the main body. Three partition plates for insects to climb are clamped in an inner portion of the main body, and the three partition plates are wave-shaped. A notch is defined at a lower middle portion of each of the three partition plates, a plurality of through holes for insect faeces to pass through are defined on a bottom of the main body, an insertion opening is defined at a lower end of an outer wall of the main body, a hinge door is rotatably disposed at the lower end of the outer wall of the main body, and the hinge door is aligned with the insertion opening. A feeding trough drawer is slidably inserted into the insertion opening, and the feeding trough drawer comprises two solid feedstuff areas and a liquid feedstuff area.

Furthermore, three clamping plate assemblies are disposed on an inner wall of the main body, each of the three clamping plate assemblies comprises two clamping plates, and the two clamping plates are symmetrically disposed. Each of the three partition plates is clamped between the two clamping plates.

Furthermore, a plurality of strip-shaped through holes are defined on each of the three partition plates, and lengths of the three partition plates are sequentially decreased from inside to outside.

Furthermore, a first separating plate and a second separating plate are respectively fixed in the feeding trough drawer, the first separating plate and the second separating plate are vertically disposed, the first separating plate separates the feeding trough drawer into the two solid feedstuff areas and the liquid feedstuff area, and the second separating plate separates the two solid feedstuff areas.

Furthermore, a fixing base and two second magnets are respectively disposed on positions, close to the insertion opening, on the inner wall of the main body. The hinge door is rotatably disposed on the fixing base, and edge portions of the hinge door are respectively adsorbed on the two second magnets.

Furthermore, a first magnet and two limiting bases are respectively fixed on a bottom portion of the feeding trough drawer, two limiting strips are disposed on an inner bottom portion of the main body, and the two limiting strips are slidably disposed in the two limiting bases.

Furthermore, ventilation openings are defined on the upper cover, and the ventilation openings are leaf-shaped. A protruding block for screwing the upper cover is fixed at a middle portion of the upper cover, an outer wall of the protruding block is connected with a plurality of protruding strips, and the plurality of the protruding strips are arranged in an annular array.

Furthermore, an opening is defined on a side wall of the upper cover, and a silicone plug is inserted into the opening.

Furthermore, an upper end of the outer wall of the main body is connected with a handle, and the handle is disposed at an upper end of the feeding trough drawer.

Furthermore, a lower end of an outer wall of the upper cover is connected with a first clamping block, and a first clamping groove is defined on an upper end of the inner wall of the main body, and the first clamping block is clamping in the first clamping groove. The lower end of the outer wall of the main body is connected with a second clamping block, a second clamping groove is defined on an upper end of an inner wall of the lower cover, and the second clamping block is clamped in the second groove.

Compared with the prior art, beneficial effects of the present disclosure are as following.

The present disclosure provides the feeding trough drawer, the partition plates, the hinge door, and the silicone plug, the silicone plug blocks the opening, so that insects, such as cockroaches, are prevented from escaping. In a process of taking out the feeding trough drawer, the hinge door cooperates the second magnets on the inner wall of the main body, the hinge door is automatically closed through a magnetic attraction principle, and then solid feedstuff of reptile feeding supplements and bread crumbs, such as calcium powder, is respectively placed in the two solid feedstuff areas, and liquid feedstuff including water is placed in the liquid feedstuff area. The insets climb on the partition plates, so that feedstuff for feeding the insects is more efficiently distributed, meanwhile, insect density per unit volume may be decreased, a breeding speed of bacteria is slowed down, and the death rate of the insects is decreased. The notch is defined on each of the partition plates, so that an enough space is reserved for easily pouring out the insects. The present disclosure additionally provides the more practical structure, which is complete in functions. The management and distribution device for insect breeding improves insect breeding environment and decreases the death rate of the insects and the time and energy cost of breeding the insects through integrating storage, feeding and breeding, faeces management, and convenient and fast putting of the insets.

Figure 1:
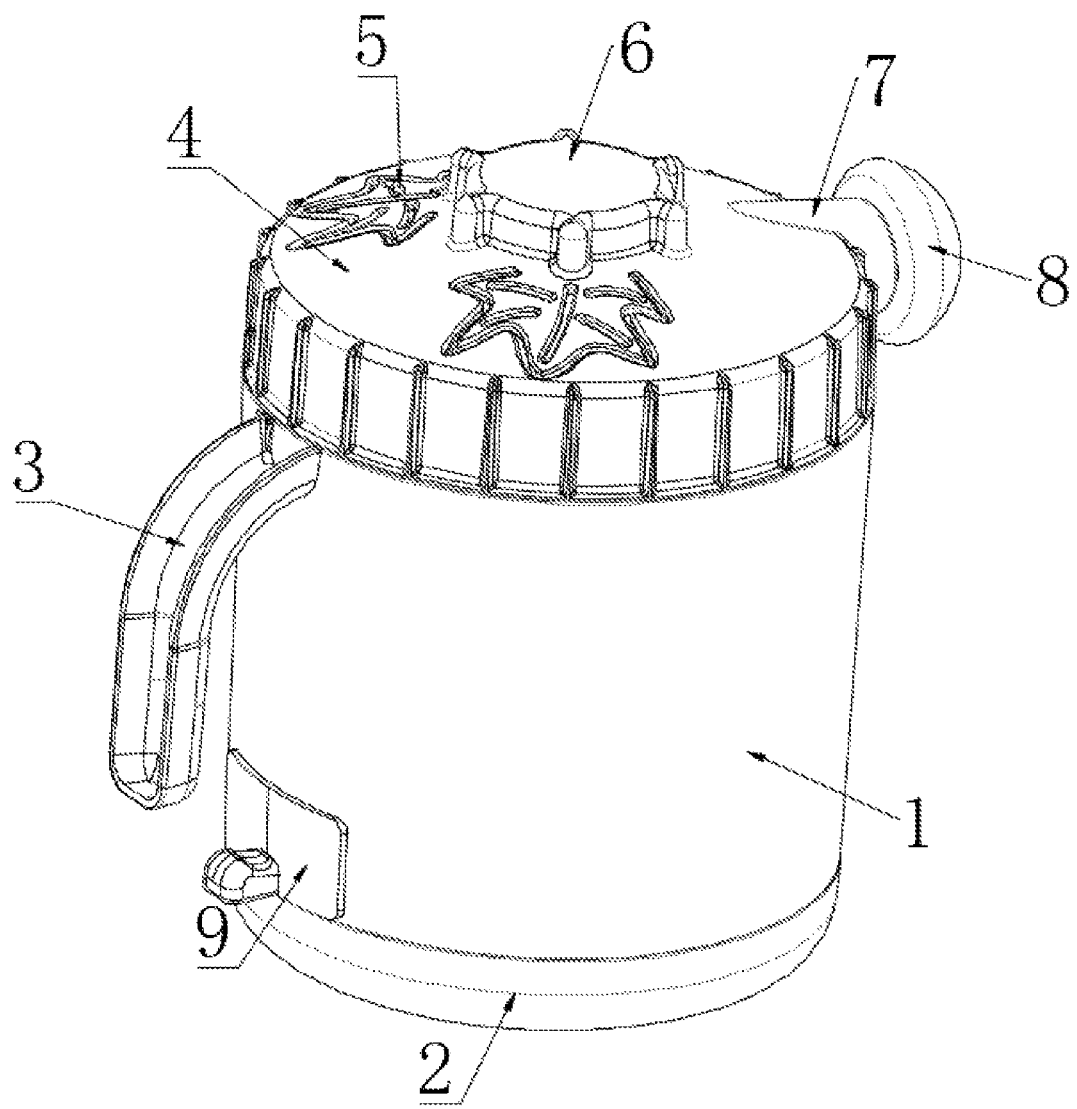
FIG. 1 is an isometric diagram of the present disclosure.

Numerals in the drawings: 1. main body; 2. lower cover; 3. handle; 4. upper cover; 5. ventilation opening; 6. protruding block; 7. opening; 8. silicone plug; 9. feeding trough drawer; 91. first separating plate; 92. second separating plate; 93. solid feedstuff area; 94. liquid feedstuff area; 95. limiting base; 96. first magnet; 10. partition plate; 101. notch; 11. clamping plate; 12. hinge door; 13. insertion opening; 14. fixing base; 15. second magnet; 16. through hole; and 17. limiting strip.

DETAILED DESCRIPTION OF EMBODIMENTS

Technical solutions in embodiments of the present disclosure will be clearly and completely described below with reference to the accompanying drawings in the embodiments of the present disclosure. All other embodiments obtained by those who skilled in the art based on the embodiments of the present disclosure without creative efforts shall fall within protection scopes of the present disclosure.

Same or similar components are labeled with the same reference numbers in different drawings. Terms such as "first", "second", "third", "upper", "lower", "front", "rear", "inner", "outer", "end", "portion", "section", "width", "thickness", "area" and the like are merely used to facilitate descriptions of the present disclosure and are not limited thereto.

Figure 2:
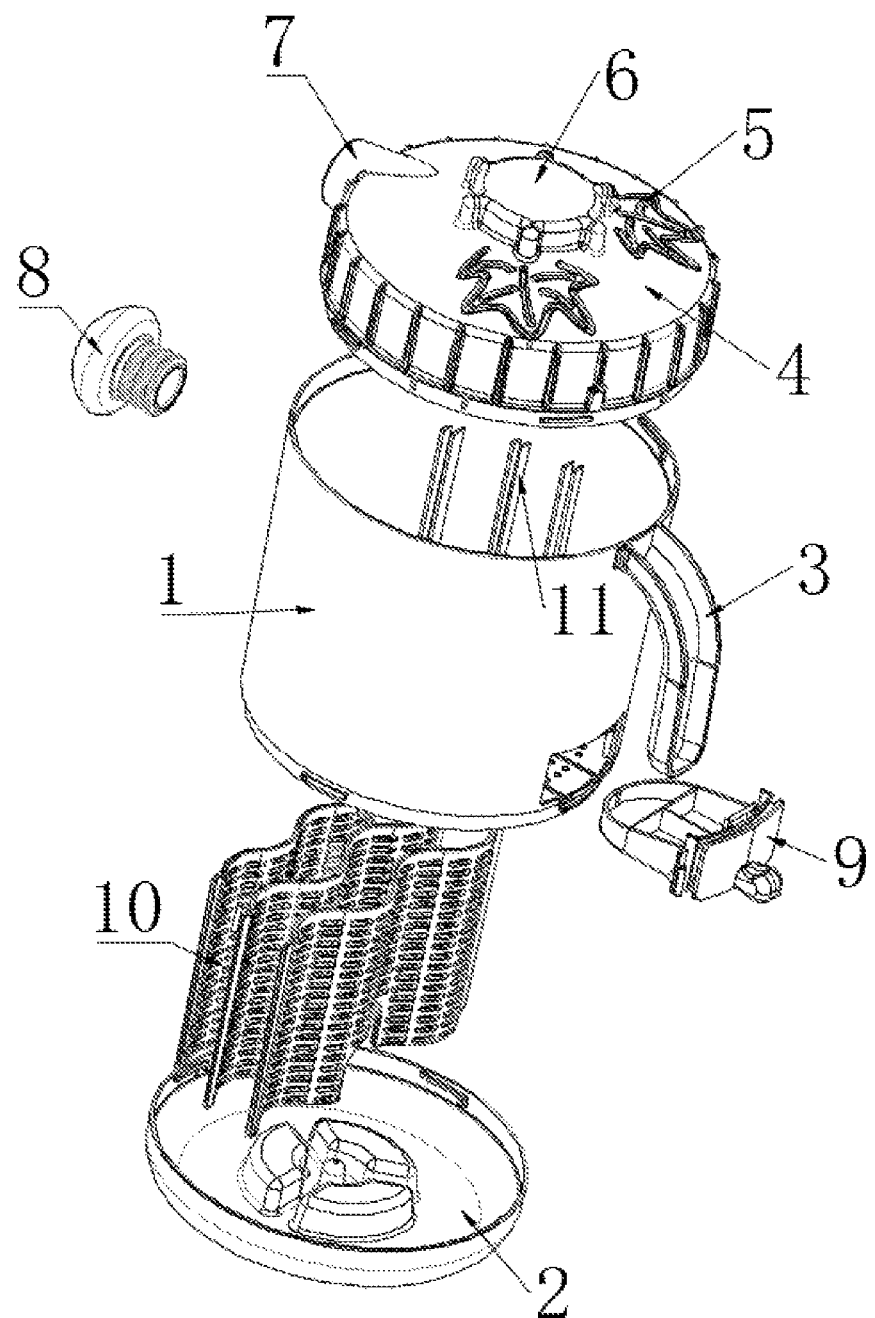
FIG. 2 is an exploded diagram of the present disclosure.
Figure 3:
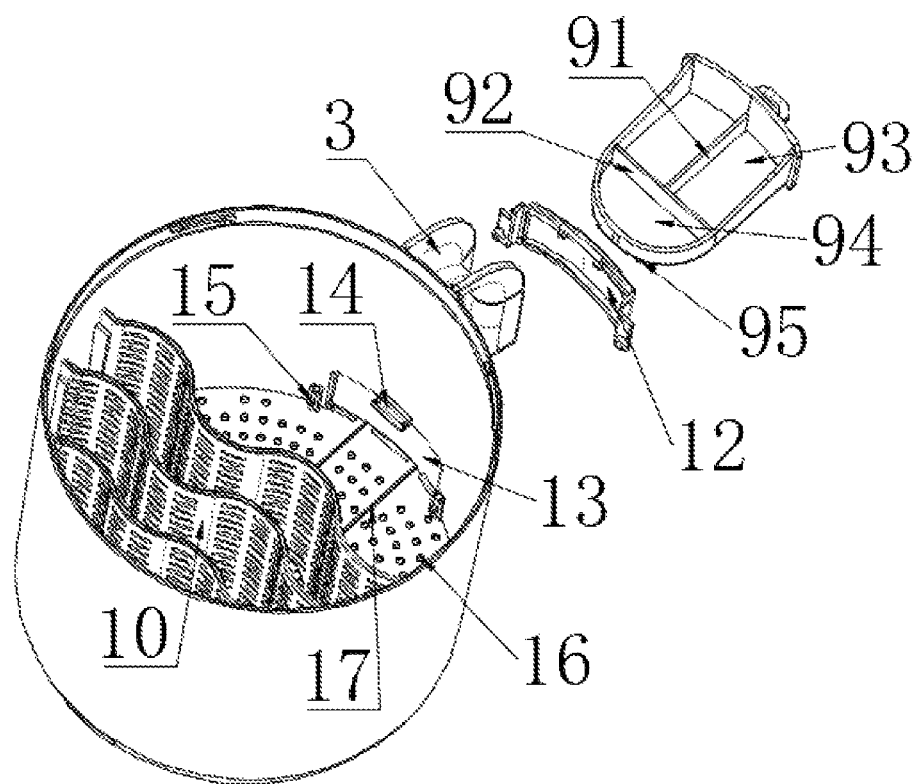
FIG. 3 is a structural schematic diagram of a feeding trough drawer, partition plates, a hinge door, a notch, a fixing base, second magnets, through holes, and limiting strips of the present disclosure.
Figure 4:
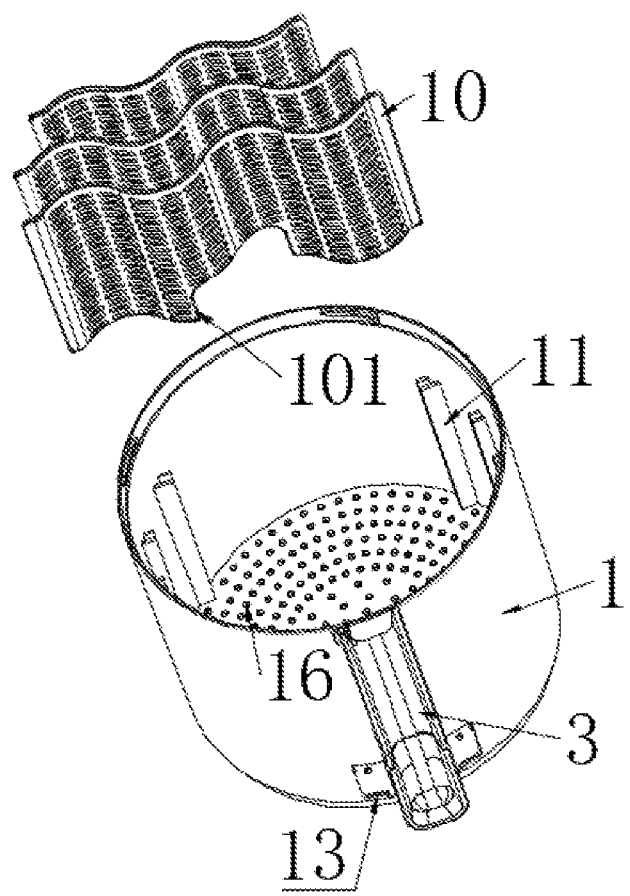
FIG. 4 is a structural schematic diagram of the partition plates, clamping plates, and the through holes of the present disclosure.
Figure 5:
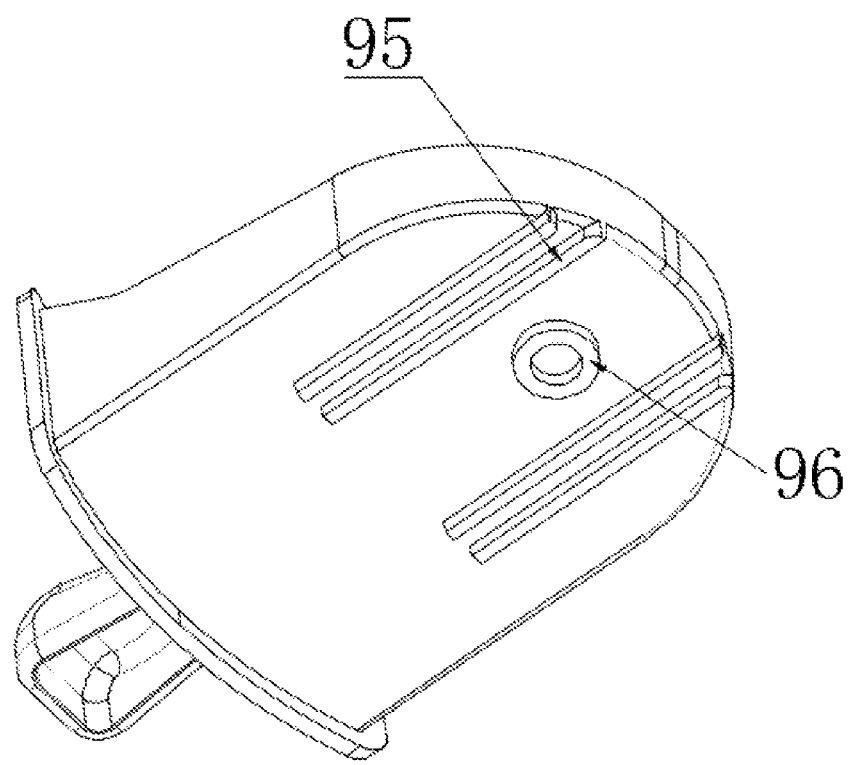
FIG. 5 is a structural schematic diagram of limiting bases and a first magnet of the present disclosure.

As shown in FIGS. 1-5, the present disclosure provides a management and distribution device for insect breeding, including a main body 1, an upper cover 4, and a lower cover 2. The upper cover 4 is clamped to a top portion of the main body 1, and the lower cover 2 is clamped to a lower end of the main body 1. The main body 1 is can-shaped. The lower cover 2 is configured to hold insect faeces, and the lower cover 3 is removed through cooperation between a second clamping block and a second clamping groove when the insect faeces need to be poured out. Three partition plates 10 for insects to climb are clamped in an inner portion of the main body 1, so that feedstuff for feeding the insects is more efficiently distributed, meanwhile, insect density per unit volume may be decreases, a breeding speed of bacteria is slowed down, and the death rate of the insects is decreased. The three partition plates 10 are wave-shaped. A notch 101 is defined at a lower middle portion of each of the three partition plates 10, so that there is an enough space for easily pouring out the insects. A plurality of through holes 16 for the insect faeces to pass through are defined on a bottom of the main body 1, and the insect faeces fall on the lower cover 2. An insertion opening 13 is defined at a lower end of an outer wall of the main body 1 and a hinge door 12 is rotatably disposed at the lower end of the outer wall of the main body 1 for loading a feeding trough drawer 9. The hinge door 12 is aligned with the insertion opening 13. The feeding trough drawer 9 is slidably inserted into the insertion opening 13, and the feeding trough drawer 9 comprises two solid feedstuff areas 93 and a liquid feedstuff area 94. Solid feedstuff of reptile feeding supplements and bread crumbs, such as calcium powder, is respectively placed in the two solid feedstuff areas 93, and liquid feedstuff including water is placed in the liquid feedstuff area 94. A sponge is placed in the liquid feedstuff area 94.

Three clamping plate assemblies 11 are disposed on an inner wall of the main body 1, each of the three clamping plate assemblies 11 comprises two clamping plates 11, and the two clamping plates 11 are symmetrically disposed. Each of the three partition plates 10 is clamped between the two clamping plates 11.

A plurality of strip-shaped through holes for the insects to climb are defined on each of the three partition plates 10, and lengths of the three partition plates 10 are sequentially decreased from inside to outside.

A first separating plate 91 and a second separating plate 92 are respectively fixed in the feeding trough drawer 9, the first separating plate 91 and the second separating plate 92 are vertically disposed, the first separating plate 91 separates the feeding trough drawer 9 into the two solid feedstuff areas 93 and the liquid feedstuff area 94, and the second separating plate 92 separates the two solid feedstuff areas 93. The two solid feedstuff areas 93 are shaped in square, and the liquid feedstuff area 94 are shaped in semicircular.

A fixing base 14 and two second magnets 15 are respectively disposed on positions, close to the insertion opening 13, on the inner wall of the main body 1. The hinge door 12 is rotatably disposed on the fixing base 14, and edge portions of the hinge door 12 are respectively adsorbed on the two second magnets 15. In a process of taking out the feeding trough drawer 9, the hinge door 12 cooperates the second magnets 15 on the inner wall of the main body 1, the hinge door 12 is automatically closed through a magnetic attraction principle.

A first magnet 96 and two limiting bases 95 are respectively fixed on a bottom portion of the feeding trough drawer 9, two limiting strips 17 are disposed on an inner bottom portion of the main body 1, and the two limiting strips 17 are slidably disposed in the two limiting bases 95. An iron block is disposed on a bottom portion of the main body 1, and the first magnet 96 is adsorbed on the iron block.

Ventilation openings 5 are defined on the upper cover 4, and the ventilation openings 5 are leaf-shaped and provides good ventilation in the main body 1. A protruding block 6 for screwing the upper cover 4 is fixed at a middle portion of the upper cover 4, an outer wall of the protruding block 6 is connected with a plurality of protruding strips, and the plurality of the protruding strips are arranged in an annular array. The protruding block 6 is convenient for screwing the upper cover 4, that is, the protruding block 6 is convenient for opening the upper cover 4.

An opening 7 is defined on a side wall of the upper cover 4, and a silicone plug 8 is inserted into the opening 7, which prevents insects, such as cockroaches, from escaping.

An upper end of the outer wall of the main body 1 is connected with a handle 3, and the handle 3 is disposed at an upper end of the feeding trough drawer 9.

A lower end of an outer wall of the upper cover 4 is connected with a first clamping block, and a first clamping groove is defined on an upper end of the inner wall of the main body 1, and the first clamping block is clamping in the first clamping groove. The lower end of the outer wall of the main body 1 is connected with a second clamping block, a second clamping groove is defined on an upper end of an inner wall of the lower cover 2, and the second clamping block is clamped in the second groove. Installation between the upper cover 4 and the lower cover 2 is facilitated.

When using the management and distribution device for insect breeding of the present disclosure, insects for breeding are placed into the main body 1, and the upper cover 4 and the lower cover 2 are clamped, the silicone plug 8 blocks the opening 7, so that the insects, such as the cockroaches, are prevented from escaping. In a process of taking out the feeding trough drawer 9, the hinge door 12 cooperates the second magnets 15 on the inner wall of the main body 1, the hinge door 12 is automatically closed through a magnetic attraction principle, and then solid feedstuff of reptile feeding supplements and bread crumbs, such as calcium powder, is respectively placed in the two solid feedstuff areas 93, and liquid feedstuff including water is placed in the liquid feedstuff area 94. Moreover, the sponge is placed in the liquid feedstuff area 94. After the feedstuff is placed, the feeding trough drawer 9 is placed into the main body 1 through the insertion opening 13, in a process of inserting the feeding trough drawer 9 into the main body 1, the feeding trough drawer 9 pushes the hinge door 12, and the hinge door 12 is automatically opened.

In a process of breeding the insects, the insets climb on the partition plates 10, so that the feedstuff for feeding the insects are more efficiently distributed, meanwhile, the insect density per unit volume may be decreases, the breeding speed of the bacteria is slowed down, and the death rate of the insects is decreased. The notch 101 is defined on each of the partition plates 10, so that an enough space is reserved for easily pouring out the insects. Moreover, faeces in the process of breeding the insects are discharged from the through hole 16 on the bottom portion of the main body 1 and fall on the lower cover 2. When the faces need to be poured out, the lower cover 2 is removed through cooperation between the second clamping block and the second clamping groove.

While embodiments of the present disclosure have been shown and described, it will be understood by those who skilled in the art that various changes, modifications, substitutions and variations can be made to these embodiments without departing from the principles and spirit of the present disclosure, which is defined by the appended claims and their equivalents.

What is claimed is:

1. A management and distribution device for insect breeding, comprising:
   a main body;
   an upper cover; and
   a lower cover;
   wherein the upper cover is clamped to a top portion of the main body, and the lower cover is clamped to a lower end of the main body; three partition plates for insects to climb are clamped in an inner portion of the main body, and the three partition plates are wave-shaped; a notch is defined at a lower middle portion of each of the three partition plates, a plurality of through holes for insect faeces to pass through are defined on a bottom of the main body, an insertion opening is defined at a lower end of an outer wall of the main body, a hinge door is rotatably disposed at the lower end of the outer wall of the main body, and the hinge door is aligned with the insertion opening; a feeding trough drawer is slidably inserted into the insertion opening, and the feeding trough drawer comprises two solid feedstuff areas and a liquid feedstuff area.

2. The management and distribution device for insect breeding according to claim 1, wherein three clamping plate assemblies are disposed on an inner wall of the main body, each of the three clamping plate assemblies comprises two clamping plates, and the two clamping plates are symmetrically disposed; each of the three partition plates is clamped between the two clamping plates.

3. The management and distribution device for insect breeding according to claim 2, wherein a plurality of strip-shaped through holes are defined on each of the three partition plates, and lengths of the three partition plates are sequentially decreased from inside to outside.

4. The management and distribution device for insect breeding according to claim 1, wherein a first separating plate and a second separating plate are respectively fixed in the feeding trough drawer, the first separating plate and the second separating plate are vertically disposed, the first separating plate separates the feeding trough drawer into the two solid feedstuff areas and the liquid feedstuff area, and the second separating plate separates the two solid feedstuff areas.

5. The management and distribution device for insect breeding according to claim 1, wherein a fixing base and two second magnets are respectively disposed on positions, close to the insertion opening, on an inner wall of the main body; the hinge door is rotatably disposed on the fixing base, and edge portions of the hinge door are respectively adsorbed on the two second magnets.

6. The management and distribution device for insect breeding according to claim 1, wherein a first magnet and two limiting bases are respectively fixed on a bottom portion of the feeding trough drawer, two limiting strips are disposed on an inner bottom portion of the main body, and the two limiting strips are slidably disposed in the two limiting bases.

7. The management and distribution device for insect breeding according to claim 1, wherein ventilation openings are defined on the upper cover, and the ventilation openings are leaf-shaped; a protruding block for screwing the upper cover is fixed at a middle portion of the upper cover, an outer wall of the protruding block is connected with a plurality of protruding strips, and the plurality of the protruding strips are arranged in an annular array.

8. The management and distribution device for insect breeding according to claim 7, wherein an opening is defined on a side wall of the upper cover, and a silicone plug is inserted into the opening.

9. The management and distribution device for insect breeding according to claim 1, wherein an upper end of the outer wall of the main body is connected with a handle, and the handle is disposed at an upper end of the feeding trough drawer.

10. The management and distribution device for insect breeding according to claim 1, wherein a lower end of an outer wall of the upper cover is connected with a first clamping block, and a first clamping groove is defined on an upper end of an inner wall of the main body, and the first clamping block is clamping in the first clamping groove; the lower end of the outer wall of the main body is connected with a second clamping block, a second clamping groove is defined on an upper end of an inner wall of the lower cover, and the second clamping block is clamped in the second groove.

* * * * *